United States Patent [19]

Provost et al.

[11] Patent Number: 5,360,736
[45] Date of Patent: Nov. 1, 1994

[54] PROCESS FOR ATTENUATED VARICELLA ZOSTER VIRUS VACCINE PRODUCTION

[75] Inventors: Philip J. Provost; David L. Krah, both of Lansdale; Paul A. Friedman, Rosemont, all of Pa.

[73] Assignee: Merck & Co., Inc., Rahway, N.J.

[21] Appl. No.: 893,295

[22] Filed: Jun. 4, 1992

[51] Int. Cl.$^5$ .............................................. C12N 5/08
[52] U.S. Cl. .......................... 435/240.21; 435/235.1; 424/230.1
[58] Field of Search ........... 424/89; 435/235.1, 240.21

[56] References Cited

U.S. PATENT DOCUMENTS

| | | | |
|---|---|---|---|
| 3,555,149 | 1/1971 | Buynak et al. | 424/89 |
| 3,660,565 | 5/1972 | Plotkin | 424/89 |
| 3,915,794 | 10/1975 | Zygraich et al. | 195/1.8 |
| 3,919,411 | 11/1975 | Glass et al. | 424/88 |
| 3,961,046 | 6/1976 | Cerini | 424/89 |
| 3,985,615 | 10/1976 | Kube | 195/1.3 |
| 4,000,256 | 12/1976 | Hilleman et al. | 424/89 |
| 4,147,772 | 4/1979 | McAleer et al. | 424/89 |
| 4,252,792 | 2/1981 | Blades | 424/89 |
| 4,273,762 | 6/1981 | McAleer et al. | 424/89 |
| 4,324,861 | 4/1982 | Kan | 435/237 |
| 4,337,242 | 6/1982 | Markus et al. | 424/89 |
| 4,338,335 | 7/1982 | McAleer et al. | 424/361 |
| 4,772,466 | 9/1988 | Allison et al. | 424/88 |
| 5,024,836 | 6/1991 | McAleer et al. | 424/89 |

FOREIGN PATENT DOCUMENTS

| | | | |
|---|---|---|---|
| 0030199 | 10/1981 | European Pat. Off. | A61K 35/76 |
| 65905A1 | 12/1982 | European Pat. Off. | A61K 39/12 |
| 2747662 | 6/1978 | Germany | A61K 39/16 |
| 48048621 | 10/1971 | Japan . | |
| 48-010523 | 4/1973 | Japan | A61K 27/12 |
| 01279843A2 | 11/1989 | Japan | A61K 9/14 |
| 1481650 | 8/1977 | United Kingdom | A61K 39/25 |
| 563175 | 6/1977 | U.S.S.R. | A61K 39/12 |

OTHER PUBLICATIONS

Brunell, 1967, "Separahon of infections Varicella-zoster..." Virology 31(4): 732-734.

Iscove and Melchers et al., 1978, "Complete Replacement of Serum Albumin..." J. E. M. 147: 923-933.

Kielian, et al., 1986, "Kinetics of endosome acidification detected..." EMBO J. 5: 3103-3109.

Iscove, 1984, "Culture of Lymphocytes and Hemopoietic..." Methods for Serum-Free Culture of Neuronal and Lymphoid Cells, pp. 169-185.

Takahashi, et al., 1974, "Live vaccine used to prevent..." The Lancet Nov. 30, 1288-1290.

Grose, et al, 1981, "Cryopreservation of varicella-zoster..." Intervirology 15: 154-160.

Buus, et al., 1984, "Chloroquine inhibits accessory cell presentation..." Acta Pathol. Microbiol. Scand. Sect. C Immunol. 92(5): 285-292 (abstract).

Hayakawa et al., J. Infect. Dis. 149, 956-967 (1984).

Hondo et al., Arch. Ges. Virus 40: 397-399 (1973).

Howell & Miller J. Clin. Microbiol. 18: 658-662 (1983).

Husson, J. Biol. Stand. 15: 385-388 (1987).

Languet et al., Comp. Immun. Microbiol. Infect. Dis. 8: 285-295 (1985).

Majer et al., Dev. Biol. Stand. 36: 285-289 (1976).

Mariner et al., Vet. Microbiol. 21: 195-209 (1990).

McAleer et al., J. Biol. Stand 8: 281-287 (1980).

Michalski et al., Infect. Immun. 14: 135-143 (1976).

Popa & Repanovici Acta Virol. 21: 280-287 (1977).

Schmidt & Lennette Infect. Immun. 12: 606-613 (1975).

Scott & Woodside J. Clin. Microbiol. 4: 1-5 (1976).

Shiraki et al., Acta Virol. 33: 565-568 (1989).

Takahashi et al., Postgrad. Med. J. 61 (Suppl. 4): 37-46 (1985).

(List continued on next page.)

*Primary Examiner*—Christine M. Nucker
*Assistant Examiner*—J. Stucker
*Attorney, Agent, or Firm*—Gerard H. Bencen; Jack L. Tribble; Paul D. Matukaitis

[57] ABSTRACT

A live, attenuated varicella zoster virus vaccine is produced with enhanced yield of VZV. The new process makes mass production of a live VZV vaccine more practical.

9 Claims, 5 Drawing Sheets

OTHER PUBLICATIONS

Yaminishi et al., Infect. Immun. 28: 536–541 (1980).
Takayama & Oya Biken J., 24: 109–118 (1981).
Boehringer Mannheim Catalog, p. 648 (1991).
DeCourcy and Storrie, Esp. Cell Res. 192, 52–60 (1991).
Cohn et al., J. Exp. Med. 129, 201–222 (1969).
Iscove et al., Exp. Cell Res. 126, 121–126 (1980).
Farrant et al., Hormonally Defined Media pp. 300–303 Fisher & Wieser (Ed). Springer–Verlby (1982).
Fazekas de St. Groth J. Imm. Methods, 57 121–136 (1983).
Muzik et al., In vitro 18 515–524 (1982).
Weiss et al., In vitro 16(7), 616–628 (1980).
Miles Inc., Catalog Description of EX-CYTE*
Mann, G. F., *Develop. Biol. Stand.*, 37, 149–152 (1977).
Wood and Minor, *Biologicals* 18, 143–146 (1990).
Enders, J. F. et al., Proc. Soc. Exp. Biol. Med. 86, 277–286 (1954).
Arbeter, A. M. et al., Pediatrics 76 Suppl. 742–746 (1976).
Physicians Desk Reference, 1991, pp. 1401–1403.
Krah, D. L. et al., *J. Vir. Method* 27, pp. 319–326 (1990).
P. J. Provost et al., *Vaccine* 9, 111–116 (1991).
Asano & Takahashi Biken J. 21: 15–23 (1978).
Bovarnick et al., J. Bacteriol. 59: 509–522 (1950).
Calnek et al., Appl. Microbiol. 20: 723–726 (1970).
de S. Lopes et al., J. Biol. Stand 16: 71–76 (1988).
de Rizzo et al., Bull. Pan. Am. Health Org. (US) 23: 299–305.

PROCESS FOR ATTENUATED VARICELLA ZOSTER VIRUS VACCINE PRODUCTION

BACKGROUND OF THE INVENTION

Varicella zoster virus (VZV) causes chickenpox and zoster (shingles). Chickenpox is a highly contagious disease that occurs in persons with no VZV immunity. More than 90% of the population is exposed during the first two decades of life. The disease is a severe threat to the immunosuppressed and to adults. In many cases, VZV becomes latent in dorsal root ganglion cells. Shingles, a painful chronic condition, occurs when VZV is reactivated from the latent state.

Prevention of chickenpox by vaccination is a desirable goal, and the institution of universal childhood vaccination with a live attenuated varicella vaccine is envisioned. The prior art has reported the propagation of VZV in various cell culture systems and the use of live, attenuated, cell-free VZV as a vaccine. U.S. Pat. No. 3,985,615 describes the production in guinea pig primary embryonic cells of the attenuated Oka strain of VZV, suitable for vaccine use. U.S. Pat. No. 4,008,317 describes the cultivation of a temperature-sensitive mutant of VZV in WI-38 cells for use as a vaccine stablilizer. Compositions useful for the maintainance of viable VZV, such as SPGA, are also known in the art.

The major limitation to commercial production of a VZV vaccine is the yield of cell-free VZV from cell culture systems known in the art. Cell-free VZV yields are improved by about a factor of 5–20 fold by application of the new process of this invention.

Thus, the present invention is a process for the production of a live, attenuated, cell-free VZV vaccine in high yield.

SUMMARY OF THE INVENTION

The present invention is a process for the production of large amounts of a live, attenuated, cell-free VZV vaccine, useful to prevent chickenpox, which comprises optimally propagating VZV in cell culture, and harvesting the virus under conditions which maximize VZV yield and stability. The steps of the optimized process comprise:

a. Culturing VZV infection-susceptible cells, selected from human diploid cells, such as MRC-5, to confluency in monolayer culture, using high culture volumes or rich culture medium, and supplying a nonmetabolizable disaccharide, such as sucrose;

b. Infecting the cells cultured according to step (a) at as close to the point of confluency as possible with as high a multiplicity of infection of VZV-infected cells as practical;

c. Maintaining the VZV-infected culture in a state of high nutrition for about 22–96 hours and harvesting at the point of peak VZV production;

d. Washing the VZV-infected culture with a physiologic solution, optionally containing a lysosomotropic agent, such as ammonium chloride or chloroquine, prior to harvesting the VZV infected cells;

e. Harvesting the VZV infected cells into a minimal volume of a stabilizing solution, and either disrupting the cells immediately or freezing the cells for later disruption;

f. Disrupting the VZV-infected cells to optimally release cell-associated VZV, and removing cellular debris, to provide a cell-free VZV preparation.

BRIEF DESCRIPTION OF THE DRAWINGS

FIG. 6. VZV Viral Antigen Yields as a Function of Input MOI.

DETAILED DESCRIPTION OF THE INVENTION

Figure 1:
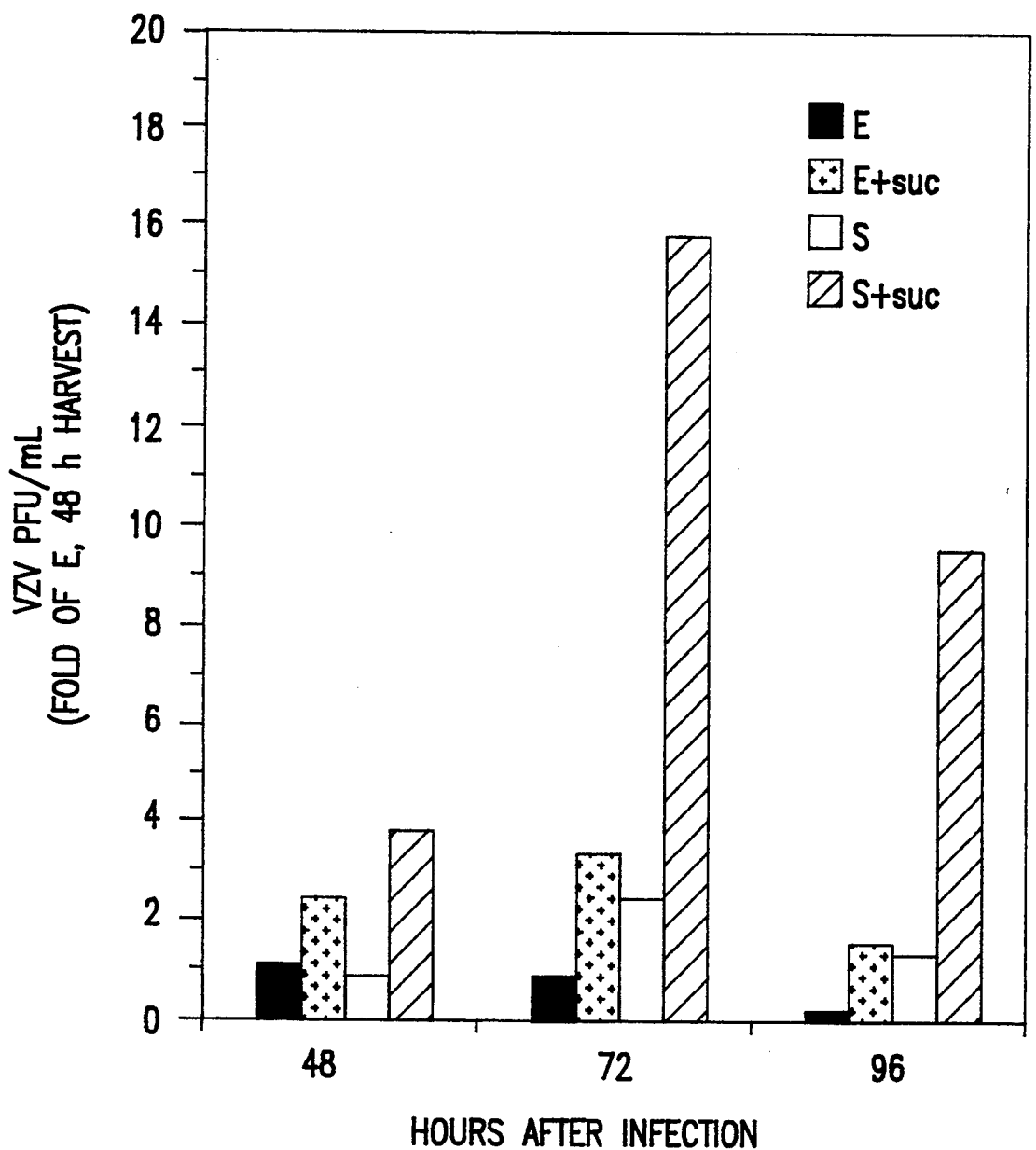
FIG. 1. VZV PFU Yields in Sucrose Supplemented Media

The novel process of this invention comprises propagating VZV in cell culture, and harvesting the resultant VZV under conditions which optimize virus yield and stability. The advantages disclosed for the production of VZV will be applicable to the production of other enveloped viruses, including herpes viruses other than VZV, measles, mumps, or rubella.

The ultimate goal of this invention is to provide a process which permits efficient production of VZV for use as a vaccine. The success of the process is measured by the yield of cell-free VZV finally achieved upon optimization of each step of the process. The yield is determined by the infectivity titer of the final cell-free VZV preparation. The infectivity titers of varicella zoster virus (VZV) preparations were obtained by an agarose-overlay or liquid overlay procedure described by Krah et al. (J. Virol. Methods, 1990, 27:319–326). Briefly, this method involves culturing MRC-5 cells, which are susceptible to VZV infection, to an actively replicating state, that is, to a point where the cells are about 50–80% confluent. Virus is then overlaid onto the cell monolayer in a minimal volume, allowed to attach to the cells and then additional growth medium is added. After several days of growth, the cells are exposed to a protein stain, and clear areas, plaques, are counted. Thus, for a known volume of viral inoculum, the number of plaque forming units (PFU) per milliliter represents a good measure of virus yield. Multiplied by the total volume of cell-free virus obtained from any given viral preparation, the total number of PFU may be calculated.

Due to variability in the assay itself, the increase in PFU obtained by any particular process optimization is reported as a ratio to some less optimized process step. This reporting of fold-increases in viral yield therefore nullifies any variability in the PFU assay itself. Ultimately, the process steps described herein cumulatively result in between about a 16–20 fold increase in VZV yields achieved using methods known in the art. This fold increase is not reported in the literature and it represents a significant contribution to the art of VZV vaccine production.

Because the VZV plaque assay is time consuming, it is not particularly amenable to in-process control. A rapid VZV antigen ELISA permits measurement of VZV antigen amounts to permit monitoring of virus growth during manufacture of live varicella vaccine. Additionally, this test can be used to estimate VZV antigen amounts in clarified, sonicated vaccine bulks, and potentially to measure antigen in filled lyophilized vaccine vials. Briefly, this assay is conducted by incubation of VZV antigen from test samples with anti-VZV serum in solution. Remaining free antibody is allowed to bind to VZV antigen immobilized on ELISA microtiter plates. The amount of antibody capable of binding to the plates is inversely proportional to the amount of antigen in the test sample. Antibody binding to the plates is quantitated by reaction with an enzyme-linked anti-human antibody and appropriate substrate to provide a colored product which is quantitated spectrophotometrically.

The VZV antigen ELISA and the VZV plaque assays should generally provide correlative data, but it should be borne in mind that the VZV antigen assay detects non-viable as well as viable VZV. Since the immune response generated by killed VZV has not been shown to be as effective as the response to live attenuated virus, the plaque assay is the critical assay for determination of viral inoculum dose for VZV vaccines. However, the antigen assay is valuable in that it provides a measure of the total antigen load being administered to a VZV vaccine recipient, it is more rapid than the PFU assay and therefore allows in-process monitoring of VZV production, and it correlates at least to the point of peak VZV PFU production allowing estimation of the optimal time for harvest.

The success of the process of this invention is incrementally enhanced by each of the following critical parameters, all of which are within the scope of this invention:

a. Culturing VZV infection-susceptible cells, selected from human diploid cells, such as MRC-5, to confluency in monolayer culture, using high culture volumes or rich culture medium to acheive a high degree of cell replication, and supplying a non-metabolizable disacchride, such as sucrose Any of a number of different cell culture systems known in the art to be useful for VZV production may be used. Thus, Vero cells, WI-38 cells, MRC-5 cells, and a number of other cell types have been used for this purpose. We have consistently used MRC-5 cells which are acceptable for production of vaccine intended for human use. It is not inconceivable, however, that cell-free VZV yields may be enhanced beyond the extent reported here if a particularly productive cell line other than MRC-5 were utilized. To the extent that such a cell line would be adaptable to use in the current process, this invention encompasses application of this process to such cells.

Comparison of cell-free, live virus yields in either sub-confluent or confluent MRC-5 cell monolayers incubated at 35° C. under an atmosphere of 5% $CO_2$ in Eagles Minimal Essential Medium (EMEM) with 2% or 10% Fetal Calf Serum (FCS) reveals the effect of cell confluency on the yield of cell-free VZV plaque forming units (PFU) (see Example 2, Table I).

Use of confluent cell-monolayers gives rise to about a 2-3 fold increase in cell-free PFU/mL over the yield achieved by infection of subconfluent monolayers whether the subconfluent cultures are actively proliferating (10% serum) or not (2% serum). Therefore, confluent but not actively proliferating cells appear to be necessary for enhanced VZV yields, in the vaccine production process.

The percentage of fetal calf serum present during vital growth does not appear to have a major effect on cell-free pfu yields. Thus, typically, during the cell growth phase, FCS is provided at about 10% while during viral growth phases of the process, FCS is provided at about 2%, whether a minimal medium, such as EMEM or EBME or a rich medium, such as SRFE-2, is used for cell growth and virus culture.

In addition to the FCS and medium, typically an antibiotic such as 50 μg/ml Neomycin, and glutamine (about 2 mM) are added to the cell culture and viral growth media.

1. Cell Planting Phase

Cell culture containers (flasks, roller bottles, or functional equivalents of these culture vessels) are seeded with MRC-5 or other diploid cells so that the initial concentration of cells is between about 10,000 and 40,000 cells/$cm^2$. The cells are fed with growth medium supplemented with about 10% fetal calf serum, gassed with 5% $CO_2$, and incubated at about 30°–37° C., and preferably about 35° C.

The cells may be planted in as small a volume as necessary to completely cover cells grown in stationary culture. A workable ratio of volume to surface area is about 0.5 mL of culture medium per $cm^2$ of growth surface. Where cells are grown in roller bottles, as little as 125 mL per 850 $cm^2$ may be adequate, but about 425 mL/$cm^2$ is preferable.

Commercially available minimal media known in the art for cell culture, such as Eagles Minimal Essential Medium (EMEM) or Eagles Basal Medium supplemented with Earle's Salts (EBME), may be used with about 10% FCS for the cell planting phase. Alternatively, a richer medium may be used to advantage in this phase. SRFE medium [Weiss, et al., In Vitro 16(7), 616–628 (1980)], available from SIGMA, is a rich medium which may be used to advantage at this stage, but a rich medium is not critical to this stage of the process.

2. Cell Growth Phase

It is critical that sufficient nutrition be provided in this phase of the process to ensure growth of cells to heavy confluency. This may be achieved by providing a large volume of minimal medium or a lesser volume of rich medium. The cells are grown at about 30°–37° C. and preferably at about 32°–35° C.

After allowing an adequate period for cell attachment and cell growth, cells may be re-fed by removing and replacing the medium and then continuing the incubation. The medium may be removed by aspiration or decantation, or any other means so long as the integrity of the cell monolayer is not compromised. For MRC-5 cells planted as described above, re-feeding may be undertaken about 72 hours after introduction of the cells into the culture vessel.

The volume of culture medium replaced may be the same as the volume used for the cell planting phase. Preferably, however, a larger volume than was used during planting is provided during the cell growth phase. This is particularly important where cells are being cultured in a minimal medium such as EMEM or EBME plus FCS. A large culture volume is one way to ensure that the cells receive adequate nutrition.

The requirement for large volume may be reduced where the medium supplied for the growth phase is a rich medium. One particularly preferred medium for this purpose is SRFE-2 (SIGMA). Use of a rich medium at this stage, rather than a minimal medium, greatly enhances the density of the cell monolayer at confluency. The enhanced cell density carries over to enhance the yield of VZV obtainable from an infected cell culture grown in enriched media. Thus, use of enriched medium during cell growth phase has given rise to about a 2–4 fold increse in final VZV yield over that achieved when cells are grown in minimal media at this stage.

In a preferred embodiment, SRFE-2 is supplemented with lipid. Any of a number of lipid supplements are useful. Thus, cholesterol rich lipids from adult bovine serum (SIGMA CHEMICAL CO.), EXCYTE lipid I or Very Low Endotoxin (VLE) lipid (MILES) were found to be beneficial as rich medium or minimal medium supplements. Commercially available soybean lipid (Boehringer Mannheim, also see Iscove et al., *J. Exp. Med.* 147, 923–933 (1978)] has proven to be a very beneficial supplement when provided at about 0.2 mg/ml. Cell densities approaching about 500,000/cm2 have been achieved using SRFE-2 plus lipid and FCS. Enhanced VZV yields are achieved when lipid is provided regardless of whether cell growth is in minimal media or enriched media. Commercially available material is supplied as a 20 mg/mL lipid, 100 mg/mL bovine serum albumin stock. This material is conveniently used at 1:100 final dilution. Final VZV yield was enhanced by about nine fold over the VZV yield from EMEM alone, and by about 3.3 fold over SRFE-2 medium alone when SRFE-2 was supplemented with about 0.2 mg/mL soybean lipid during the cell growth phase.

3. Pre-Infection Phase

We have discovered that the final yield of VZV may be further enhanced when cultured cells are exposed to to a non-metabolizable, non-toxic disaccharide at an optimal concentration, prior to VZV infection. One very successful embodiment provides about 20–60 mM sucrose about 72 hours after the cells are introduced into the culture vessel, and preferably about 24 to 96 hours before infection of the culture with VZV. As a practical matter, provision of about 50 mM sucrose in the re-feed medium of step 2 above meets these criteria and reduces the number of sterile manipulations required by effectively making this and the previous steps concurrent.

Other disaccharides, including lactose, cellobiose, and maltose also enhance the final VZV yield, but sucrose is preferred. Monosaccharides tested, such as fructose and ribose did not enhance VZV yield (ribose may even be toxic). It appears that the disaccharides are being concentrated in the lysosmes of the growing cells, swelling these to form vacuoles [DeCourcy and Storrie, *Exp. Cell Res.* 192, 52–60 (1991)]. This dissacharide effect on VZV yield may be due to attenuation of lysosomal damage of VZV. In addition to disaccharides, tri- and tetrasaccharides may be expected to have beneficial effects as Cohn and Ehrenreich [*J. Exp. Med.* 129, 201–222 (1969)] noted identical vacuolization when these higher sugars or sucrose were fed to macrophages, as long as the sugars were not metabolized by the cells.

b. Infecting the Cells Cultured According to Step (a) at as close to the Point of Confluency as Possible with as High a Multiplicity of Infection of VZV-Infected Cells as Practical We have found, by repeated experiments, that on average, cells allowed to sit for 48 hours after becoming confluent yield only about 50% of the VZV PFU/ml as compared with the yield when freshly confluent cells are infected with VZV. Thus, it is important to time the introduction of the VZV inoculum to coincide as closely as possible with confluency. Unfortunately, confluency is a parameter which varies according to the type of medium, the cell type being cultured, and other culture conditions used. For MRC-5 cells planted according to step (a)(1) above, the cells are typically infected at the point of reaching confluency.

The varicella-zoster virus (VZV) is preferably the Oka strain of attenuated virus described in U.S. Pat. No. 3,985,615 and which is on deposit with the ATCC. This virus is adapted to growth in guinea pig embryo cell cultures and human diploid lung fibroblast cell cultures (e.g., MRC-5 cells).

A stock of infectious, viable, varicella-infected cells may be prepared by infecting MRC-5 cells at an MOI of about 1:125, maintaining the infected cells to allow for vital replication, trypsinizing the cells, and using the released cells immediately as a working seed or stored for later use and PFU quantitation by slowly freezing with a cryoprotectant such as DMSO or glycerol at about $10^7$ cells/ml. The frozen, VZV infected cell-stock can be thawed and added to a confluent cell-culture to initiate VZV infection.

Alternatively, VZV-infected cells may be lyophilized according to the method described by Hondo et. al., [*Archiv fur die gesamte Virusforschung* 40, 397–399 (1973)] which allows for long-term 4° C. storage of the lyophilized inoculum. It is also possible to use cell-free VZV as an inoculum, but due to losses in virus yield upon harvesting, use of a cell-bound inoculum is preferred.

Another possibility for production of the virus-infected seed stock is to initiate cell growth for virus seed production before production cell planting. At the point of seed-cell infection with VZV infected cells, planting of production cells may be initiated to achieve confluency at the same time that the virus seed reaches peak VZV titers. Less optimally, but more conveniently, the seed cells and the bulk cells may all be planted at the same time, in a small volume of culture medium (about 125 mL per 850 $cm^2$ roller bottle). After about two-three days growth, the bottles for VZV seed production are increased in volume to about 425 mL, or refed with rich medium, to allow for growth to confluency. The production cells are left, relatively dormant, in a small volume of minimal medium (including about 10% FCS) until about two days before working seed cells are infected with VZV infected cells. At this point, the production cell volume is increased to about 425 mL or refed with rich medium, such as SRFE-2 plus an optimal amount of soybean lipid and fetal calf serum. The production cells will then grow to heavy confluency. Two days after refeeding the production cells, the working seed cells, now at confluency, are infected with VZV-infected cells at an MOI of 1:125 or higher, and VZV replication is allowed to continue for about two to three days. By the time of peak VZV production in the seed cultures is reached, the production cells will have reached confluency. Then the seed cells are harvested and added to the production cells.

Whatever the timing of seed production, at an appropriate time after VZV infection, the medium is aspirated from the VZV infected seed culture, the VZV-infected seed is harvested by trypsinization (about 0.25% trypsin) or other non-disruptive means, and the production cell cultures are infected at a known MOI.

Schmidt, N. S. and Lennette, E. H., [*Inflection and Immunity* 14, 709–715 (1976)] noted the importance of high MOI for high VZV yield, but made no strict comparison with low MOI infection. The instant invention makes precisely this comparison.

Cells are infected with VZV by removing the growth medium from the cell cultures and replacing it with fresh medium containing a known amount of VZV infected cells prepared as described above. The virus stock is preferably titered for varicella plaque forming units (PFU's), and the recipient cells are counted to allow quantitation of the multiplicity of infection (MOI). MOI's are expressed as the ratio of VZV infected cells in the inoculum to the number of non-infected monolayer cells in culture. Thus, an MOI of 1:10 is high, while 1:625 is low. A high MOI is desirable, but as a practical matter, good VZV yields can be achieved with an MOI as low as 1:125.

MOI's of between 1:7 and 1:625 yield between about 500,000 PFU/mL at the high MOI down to about 100,000 PFU/mL at the low MOI end (see Table 3 of Example 5). The higher the MOI, the shorter the required incubation time to reach peak PFU and the greater the yield. Thus, about a 5-fold range in final PFU may be achieved depending on the MOI and time of harvest.

c. Maintaining the VZV-Infected Culture in a state of high nutrition for about 22-96 Hours and Harvesting at the Point of Peak VZV Production The cultivation of the VZV-infected cells is continued for approximately 22 to 96 hours after infection. It is critical that adequate nutrition be maintained at this stage of the virus growth. Either provision of high culture volumes of a minimal medium such as EMEM plus about 2-10% FCS, or a lesser volume of rich medium is desirable. Most preferably, SRFE-2 plus 2-10% FCS is provided without the addition of lipid supplementation. The lipid has been noted to reduce VZV yield when included at this stage.

Figure 5:
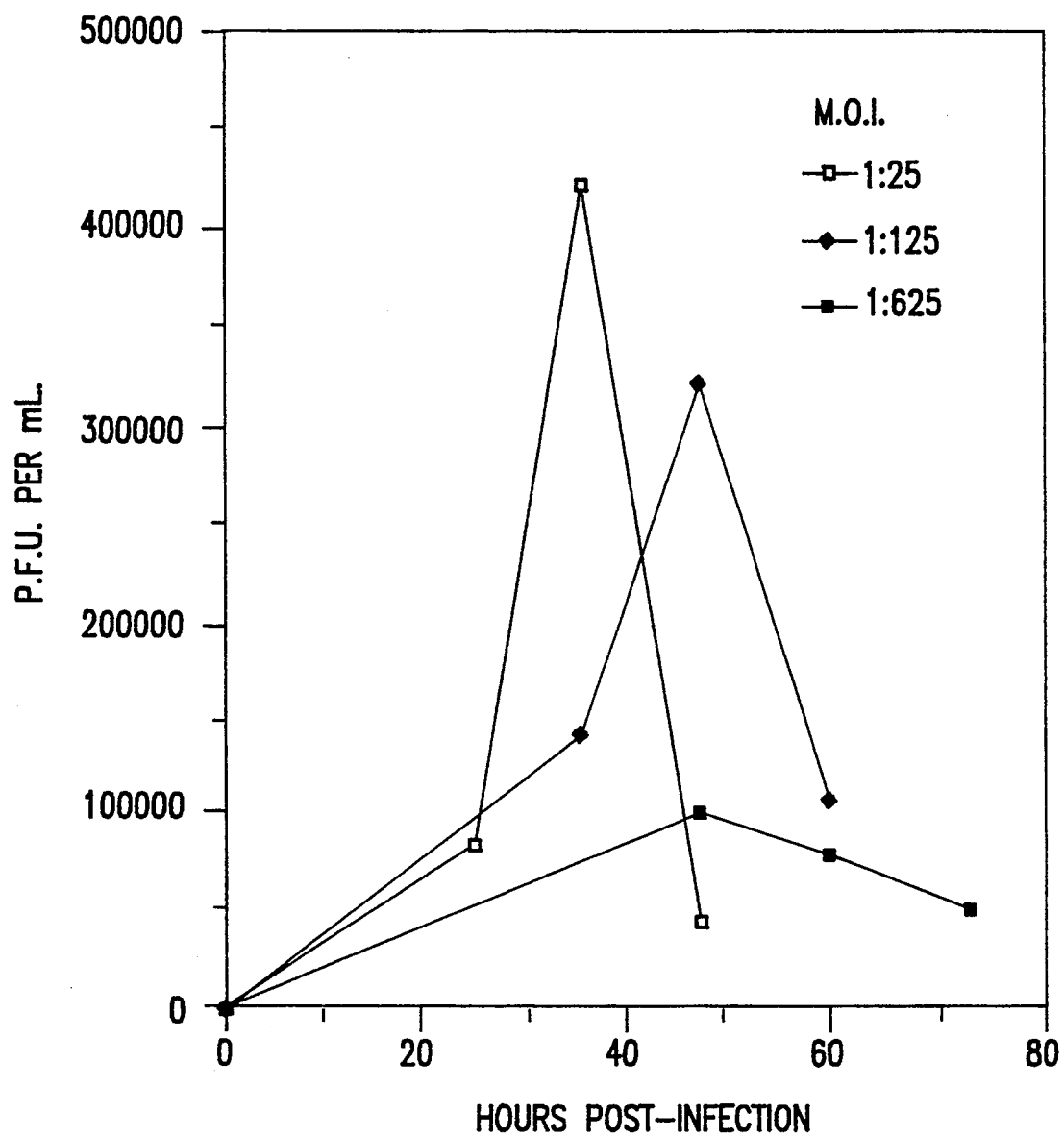
FIG. 5. Effect of Input Cell-Associated MOI on Cell-Free VZV Yields.

During the 22-96 hours of post-infection culture, VZV replicates in the cells which have been infected and spreads to infect adjacent cells. However, old infected cells will not give recoverable cell-free PFU's. The VZV growth curve and subsequent decline can be quite sharp. Therefore, correct timing of the point of harvest is a critical parameter for maximizing infectious VZV yield, and can be accurately reproduced by maintainance of tight control of input MOI, nutrition, and incubation time from production run to production run. In addition, the rapid VZV antigen ELIZA may be employed to optimize time of harvest as infectious VZV production correlates with VZV antigen production, at least until the point where virus death begins to occur (see FIGS. 5 and 6).

For VZV infected MRC-5 cells harvested about 72 hours post-infection, where each of the foregoing steps was optimized, (i.e. growth in rich medium and pre-infection exposure of the cells to 50 mM sucrose for 72 hours) the final yield of cell-free VZV was increased by about sixteen fold over the yield achieved in minimal medium and viral harvest at 48 hours, and by an even greater margin than when harvest is at 96 hours (see EXAMPLE 8, FIG. 1). The yield of VZV under the same optimized conditions was only about four-fold over the minimal medium yield when the virus was harvested 48 hours post-infection, but was still greatly improved over the minimal medium yield at 96 hours. Thus, virus yield is much greater and virus death is greatly reduced in rich medium and there is not such a steep dropoff of viral yield over time. The MOI also becomes less critical in rich medium.

d. Washing the VZV-Infected Culture with a Physiologic Solution, Optionally Containing a Lysosomotropic Agent, such as Ammonium Chloride or Chloroquine, Prior to Harvesting the VZV infected Cells To remove serum, lipid, and cellular debris from the culture, the monolayer culture is washed with a physiologic buffer which does not lyse the cells. Phosphate buffered saline (PBS) is quite acceptable for this purpose. The cells may be washed several times and the wash solution decanted, aspirated or removed by any other means, so long as the integrity of the monolayer is not compromised.

If the cells are chemically released from the growth vessel, they should be concentrated by centrifugation, and the physiologic buffer replaced with a stabilizing solution.

Provision of ammonium chloride or choloroquine prior to cell harvest has been found to improve final VZV yields. Kielian et al. [*EMBO J.* 5, 3103-3109 (1986)] used ammonium chloride to control the internal pH of cellular endosomes where infecting viruses apparently spend some portion of their intracellular life. Possibly the mechanism of increased VZV yield upon exposure of cells to lysosomotropic agents is related to induction of a less harsh endosomal environment. The pre-infection loading of cells with non-toxic, non-metabolizable disaccharides, such as sucrose, and the exposure of cells to ammonium chloride or chloroquine, may therefore be acting by similar mechanisms. In any event, the observation has been confirmed empirically that final VZV yields are enhanced when ammonium chloride is provided at a final concentration of between 1-100 mM, and most preferably in the range 20-50 mM, and is preferably provided at about 4° C. for from about 25-50 minutes, before cell disruption. A second lysosomotropic agent, chloroquine, at a concentration of about 230 $\mu$M, likewise increases recovery of VZV pfu/ml.

e. Harvesting the VZV infected cells into a minimal volume of a Stabilizing Solution, and either disrupting the cells immediately or freezing the cells for later disruption Once the VZV-infected cells have been washed, they may be harvested by scraping, if the growth vessel permits this, or by detaching the cells chemically. Enzymatic release of the cells is less desirable as residual enzyme may diminish viral yield once the cells are disrupted. As noted above, if the cells are released into physiologic saline, the cells are concentrated by centrifugation and the physiologic saline is replaced with a minimal volume of VZV stabilizing solution. A good volume to surface area of cell growth is about 40 mL of stabilizer per 850 cm$^2$.

Viral stabilizers are known in the art. Thus, stabilization with 5% sucrose in phosphate buffered saline is suggested in U.S. Pat. No. 3,985,615, while other reports recommend more complex stabilizers such as SPGA.

After the VZV-infected cells have been resuspended in a stabilizing solution, the cells may be disrupted immediately, or in the event that large quantities of VZV are being prepared, frozen at −70° C. for later processing. The VZV yield per cm$^2$ of cells grown will be slightly greater if the cells are disrupted immediately, but the freezing step usually does not incur a loss of more than 10% of the yield obtained by immediate processing.

f. Disrupting the VZV-Infected Cells to Optimally Release Cell-Associated VZV, and Removing Cellular Debris, to provide a cell-free VZV preparation As described above, preferably the culture medium is removed from the cells prior to disruption and replaced with a minimal volume of VZV stabilizer into which the cells are scraped or otherwise liberated. The cell suspension is chilled to 0°–4° C., and the cells are then disrupted by an appropriate means, such as sonication, DOUNCE homogenization, other types of shear which are more scalable than DOUNCE, or a combination of these techniques.

We have confirmed that sonication alone does not provide the best recovery of cell-free VZV. In fact, where DOUNCE homogenization is used as an initial disruption step, followed by centrifugation, retention of the supernatant as supernatant I, followed by sonication of the pellet and centrifugation to obtain supernatant II, the VZV yield of the disruption is greatly enhanced. The combined yield of supernatant I and II has been as high as four times the yield when sonication alone is used as the disruption technique.

Following cellular disruption, removal of cellular debris is accomplished by centrifugation, filtration, or any other means known in the art to remove cell debris while leaving VZV unharmed. The cell-free virus preparation is then diluted with stabilizing solution and subdivided for use as a vaccine. Preferably, for long term storage, the VZV is lyophilized by one of the methods known in the art.

To summarize, approximate potential yield increases by following the optimized steps of this process, as compared with VZV production by cell growth in minimal media, are reported below:

| Process Step | Fold PFU Increase |
|---|---|
| Medium/Supplements: | |
| 1. MOI | 2–5 |
| 2. Confluency of cells | 2–3 |
| 3. SRFE-2 Medium + Lipid | 2–3 |
| 4. Sucrose in pre infection phase | 2–5 |
| 5. Optimal medium volume | 1–2 |
| Net potential increase for combined medium/stabilizer supplements and optimized infection conditons | $\geq 8$ |
| Observed increase for combination of 3, 4, and 5 in roller bottles | 16 |
| 6. Combined shear/sonication for release of cell-bound VZV | 1.5 |
| Total potential increase over unoptimized process | $\geq 18$ |

Utility of this Process for Vaccine Production

The utility of attenuated, cell-free VZV as a vaccine to prevent chickenpox has been demonstrated. Multiple clinical studies have conclusively proven this utility, and such proof is now part of the prior art [see for example *Pediatrics* 88 (3) 604–607 (1991); Pediatrics 87, (5), 604–610 (1991)]. Thus, the tremendous contribution that this invention makes to the art is that it provides a highly efficient process for high yield production of live, attenuated VZV. Virus prepared according to this invention may be formulated as a vaccine according to methods known in the art, and administered according to regimens by now well established. For example, the live, attenuated, cell-free VZV product of this invention may be diluted into stabilizer, filled in bottles, lyophilized in unit doses such upon storage at about 4° C. or lower, a dose of about 1000 PFU will be available at the time of use. The VZV vaccine produced according to the process of this invention may be used in unit dose formulations to inoculate humans to induce immune-responses protective against infection by virulent strains of VZV. Preferably, at a minimum, a dose of about 2000 PFU/ml (1000 PFU/0.5 mL dose) is administered subcutaneously or intramuscularly. Doses as high as a total of 15,000 to 20,000 PFU have been administered and are acceptable.

By providing an optimized process for the production of an attenuated VZV virus, this invention makes it possible to apply what is known in the art to formulate a vaccine for boosting anti-VZV immune responses to prevent chickenpox.

The following examples are provided for the purpose of illustrating the present invention and should not be construed as limitations on its scope.

EXAMPLE 1

Assay for VZV Yield Determination

The infectivity titers of varicella zoster virus (VZV) preparations were estimated using the agarose-overlay or liquid overlay procedure described by Krah et al. (*J. Virol. Methods*, 1990, 27:319–326). The assay is performed as follows:

MRC-5 cells are seeded in 60-mm tissue culture plates at $6 \times 10^5$ cells in 5 mL volumes of BME (Basal Medium Eagle with Hanks' balanced salts solution) with 100 mg/L galactose, 50 µg/mL neomycin, 2 mM L-glutamine, and are incubated at 35° C. in a 5% $CO_2$ atmosphere. After incubation for 24–48 hours, the cells reach 50–80% confluency. The growth medium is removed by aspiration, and cells are infected with 100 µl of VZV solution diluted in appropriate virus diluent, such as SPGA buffer, or liquid maintainance medium (LMM). SPGA buffer contains 7.5% (w/v) sucrose, 11 mM potassium phosphate, 0.1% (w/v) sodium glutamate and 1% human serum albumin. Virus is allowed to attach for $\geq 1$ hour at 35° C. in a 5% $CO_2$ atmosphere The VZV-infected cell cultures are then overlaid with 5 mL agarose overlay medium (AOM) or liquid maintainance medium (LMM). Agarose overlay medium is a mixture of two solutions, liquid overlay medium (LOM) and agarose solution. LOM contains minimal essential medium with Earle's salts (MEN), 2% heat-inactivated fetal calf serum, 50 µg/mL neomycin sulfate and 2 mM L-glutamine. Agarose solution is prepared by heating 4.5 g of low gelling temperature agarose in 100 mL MEM for 15 min at 121° C. and allowing the solution to cool to 45° C. AOM is prepared by mixing one volume of agarose solution with 4 volumes of a 1.25 x concentrate of LOM at 45° C. The plates are cooled to 23°–25° C. to permit the AOM to solidify. The cultures are incubated to allow plaque development. After 6–7 days, plates which received LOM are overlaid with 5 mL of phosphate-buffered saline (PBS) and rimmed with a glass Pasteur pipette to loosen and remove the agarose. Medium is aspirated from plates which received LMM, and plaques are visualized by staining cells with a solution of 0.2% (w/v) Coomassie Blue R-250 in ethanol-1% acetic acid. Plaque counts are the average of 4–5 replicate plates and expressed as plaque-forming units per mL (PFU/mL).

Because of potential variability in the assay, enhancements of VZV yield are reported relative to unoptimized conditions assayed identically

EXAMPLE 2

VZV Yield as a Function of Cell Confluency at Infection

MRC5 cells were plated at $4 \times 10^6$ cells/150 cm$^2$ and allowed to grow for 3 days in Earle's salts supplemented with Eagles Basal Medium (EBME) in the presence of 10% Fetal Calf Serum (FCS). Upon reaching a subconfluent cell density of about $12 \times 10^6$ cells/150 cm$^2$, the cells were re-fed with fresh EBME supplemented either with 2% FCS or 10% FCS. At this point, the subconfluent cells were allowed to grow further, either in the presence or absence of VZV infection (MOI=1:125), and the increase in cell density and virus yields after 48 hours were monitored. It was found that uninfected cells in 2% FCS increased in density by only 33% while increasing by 92% in 10% FCS. Cells in the Infected cultures did not increase in number. As shown in table I, the virus yields from the subconfluent cells were not affected by the capacity for cell replication in the cultures, whether it was minimally (2% FCS) or maximally (10% FCS) supplemented with FCS.

Other cell cultures were grown an additional 2 days in 10% FCS to about $20 \times 10^6$ cells/150 cm$^2$ flask (a confluent condition), and then re-fed with fresh EBME supplemented either with 2% FCS or 10% FCS and were either infected with VZV (MOI 1:125) or left uninfected. The increase in cell density and virus yields were monitored after 48 hours. It was found that uninfected cells in 2% FCS had not increased in density while cells in 10% FCS had increased by only about 15%. Thus, neither condition was capable of much cell replication. Virus yields in either 2% FCS or 10% FCS were similar and both were increased by about three fold over the yield from cells infected at subconfluency (see table I). Thus is established the preferential use of freshly confluent cell monolayers as opposed to actively replicating subconfluent cell monolayers for optimal yields of cell-free VZV.

TABLE I

| State of Cell Monolayer at infection | % FCS during virus growth | Cell-Free PFU/mL Experiment A | Cell-Free PFU/mL Experiment B | Cell Replication Potential during Virus Growth |
|---|---|---|---|---|
| Sub-Confluent | 2 | 44,000 | 30,000 | 33% |
| Sub-Confluent | 10 | 33,000 | 27,000 | 92% |
| Freshly Confluent | 2 | 119,000 | 117,000 | 0% |
| Freshly Confluent | 10 | 123,000 | 100,000 | 15% |

EXAMPLE 3

Comparison of VZV Yield from Freshly Confluent and Aged Confluent Cell Cultures Roller bottles (850 cm$^2$) were seeded with MRC-5 cells at a concentration of approximately 26,500 cells/cm$^2$. All cells were grown in EBME medium containing 10% (v/v) fetal calf serum (FCS$_{10}$) in a 5% CO$_2$ atmosphere at 35° C. The flasks were divided into two groups, based on the time of infection with VZV. Group I cells were grown for 5 days, at which time the cell monolayers were confluent. At that time, the medium was removed and the cells were infected with cell-associated VZV at an MOI of 1:125, suspended in EMEM+2% FCS. Additional medium was added and cells were incubated for another 48 hours. Group II cells were maintained for an additional 48 hours prior to infection at an MOI=1:125.

The production of VZV by Groups I and II cells was determined as follows: medium was removed from the roller bottles and cells were rinsed with phosphate buffered saline, scraped with glass beads in equal volumes of stabilizer and chilled to 4° C. The cold cell suspensions were disrupted by sonication. Cell debris was removed from virus by low speed centrifugation ($325 \times g$ for 10 minutes) and the vital supernatant was retained. VZV production was measured by the plaque assay. As shown in Table 2, an increase in yield approaching 2-fold was obtained when freshly confluent cell monolayers were infected with VZV.

TABLE 2

| Condition | Experiment 1 | Experiment 2 PFU/mL |
|---|---|---|
| Freshly Confluent | 121,000 | 190,000 |
| Aged Confluent | 82,000 | 85,000 |

EXAMPLE 4

Effect of Culture Volume on VZV PFU/ml Yield

MRC-5 cells (10 million) were seeded in 125 mL volumes of EBME, 10% FCS, 50 µg/mL neomycin, and 2 mM L-glutamine in 850 cm$^2$ roller bottles, and incubated at 35° C. for 3 days. Three hundred milliliters of fresh medium was added and cultures were returned to incubation at 35° C. for 4 additional days. Medium was then removed and replaced with 125 or 425 mL of EMEM, 2% heat inactivated FCS, 50 µg/mL Neomycin, and 2 mM L-glutamine. VZV-infected MRC-5 cells were added (MOI about 1:125), cultures were gassed with 5% CO$_2$, and returned to incubation at 35° C. for 46 h. Medium was removed, cells were washed 4 times with 100-mL volumes of PBS, and scraped, with the aid of glass beads, into 43-mL volumes of stabilizer. Cells were frozen at −70° C. Cell-free virus was prepared by sonication. Amounts of infectious virus in clarified (by centrifugation) sonicates were measured in the VZV plaque assay.

| Results: | |
|---|---|
| Medium volume (mL) | VZV PFU/mL* |
| 125 | 55,000;45,000 |
| 425 | 153,000;103,000 |

*Results from duplicate cultures

Conclusion: The use of the higher medium volume results in about a 2-fold increase in infectious VZV yields from MRC-5 cell cultures.

EXAMPLE 5

Effect of VZV MOI on VZV PFU/ml Yield

Roller bottles were seeded with MRC-5 cells and grown to confluency. The growth medium was removed and cells were infected with VZV at varying MOI's. The production of VZV by the infected cell cultures was determined using the plaque assay by harvesting periodically and assaying as in Example 1. As shown in Table 3 and in FIG. 5, recovery of cell-free, infectious VZV was greater and achieved in a shorter incubation period when higher MOI's were employed. Peak antigen levels are also achieved more rapidly with higher MOI. At very low MOI, such as 1:625, the antigen production is delayed and suboptimal (see FIG. 6).

TABLE 3

Effect of Input Cell Associated MOI on Cell Free VZV Yields from Monolayer MRC-5 Cultures

| MOI | Cell Free VZV Titer (PFU/mL) × $10^{-3}$ Time of Harvest | | | |
|---|---|---|---|---|
| | 22 hrs | 42 hrs | 60 hrs | 37 hrs |
| 1:25 | 100 | 450 | 50 | nd |
| 1:125 | nd | 150 | 325 | 100 |
| 1:625 | nd | nd | 100 | 90 |

EXAMPLE 6

The Increased Stability of VZV in a Stabilizer at −20° C.

Figure 3:
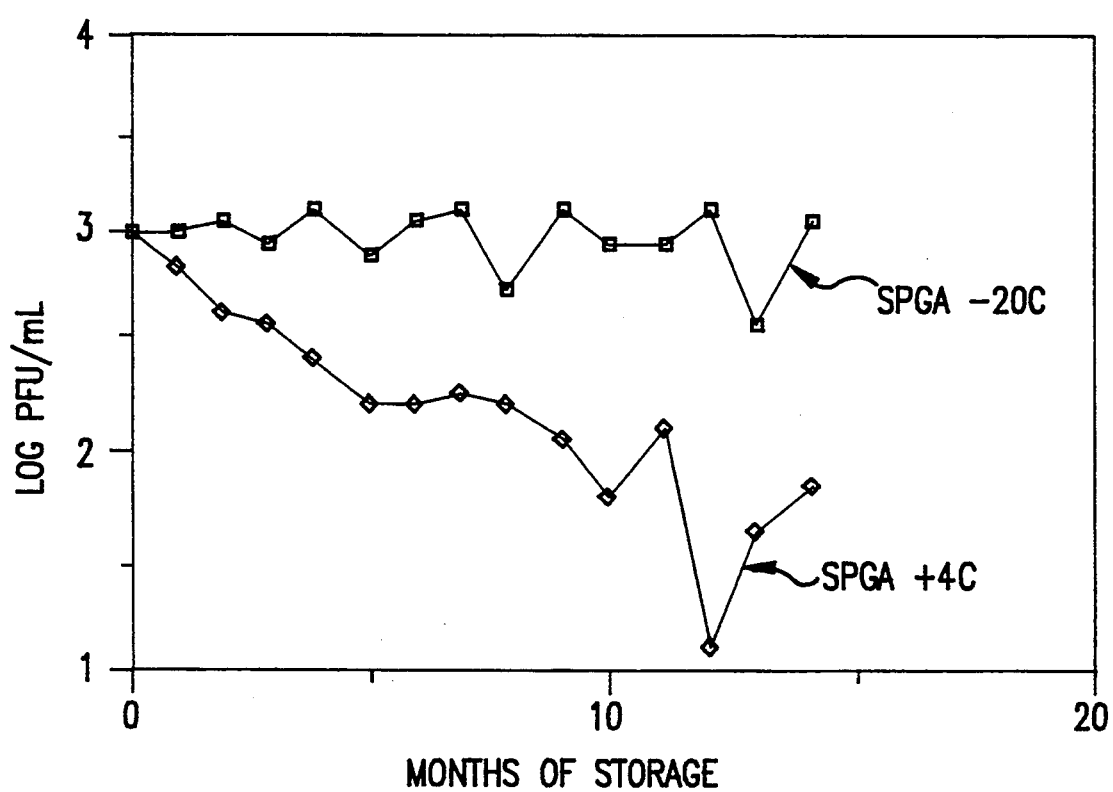
FIG. 3. VZV Stability in SPGA Stabilizer at $-20°$ C. or $4°$ C.

Infected cell cultures were sonicated in SPGA were washed with phosphate buffered saline. Cell-bound virus was then liberated by sonication and the cell-debris was removed by centrifugation. The concentration of cell-free virus was adjusted to a known PFU/mL concentration, and aliquots of the virus in stabilizer were lyophilized and stored at 4° C. or −20° C. At one month intervals over a total of 14 months, samples were reconstituted and the remaining PFU/mL titer was determined. The results of this experiment are depicted in FIG. 3.

The substantial advantage for VZV stability obtained by storage at −20° C. rather than at 4° C. is evident.

EXAMPLE 7

Effect on Final VZV Yield of Amount and Timing of Sucrose Addition During Pre-Infection Phase of Cell Growth 1. Cell Planting Phase MRC-5 cells (5 mL) were planted at a concentration of 120,000 cells/mL (600,000 cells total) on 60 mm plates in EBME medium containing 10% FCS, 50 µg/ml neomycin, 2 mM L-glutamine, and incubated at 35° C. under 5% $CO_2$.

2. Cell Growth/Pre-Infection Phase

The cells were confluent on the third day post-planting. The planting medium was aspirated from 48 plates and was replaced with 8 mL volumes of growth medium containing either EBME or SRFE-2 supplemented with 10% FCS, 50 µg/mL neomycin, 2 mM L-glutamine, and 0.2 mg/mL soybean lipid/1 mg/ml BSA, either with or without 50 mM sucrose. After addition of the fresh growth media, the cells were incubated for an additional 3 days at 35° C. under 5% $CO_2$.

3. VZV Infection

The medium was then removed from each plate and replaced with 8 mL of EMEM in place of EBME and SRFE-2 in place of SRFE-2 plus soybean lipids. The FCS was reduced to 2% for all plates, but the other supplements, neomycin, glutamine, and sucrose was as during the growth phase. Each plate then received 333 µL of a 1:16 dilution of VZV infected cells (47,000 PFU/mL) in EMEM, 2% FCS, neomycin, glutamine.

The VZV was allowed to replicate at 35° C. under 5% $CO_2$ for two days, and then the media from 2 plates from each different condition was removed. The cells were washed four times with PBS. The cells were scraped into 1.2 mL/plate of ice-cold stabilizer. The harvest from the duplicate plates was pooled in 50 mL conical centrifuge tubes and frozen at −70° C.

The same procedure as described in the preceeding paragraph was repeated for two plates from each condition on the third, fourth and fifth days post-VZV infection, and the pooled harvest from each set of two plates was stored at −70° C.

Each cell harvest prepared as described above was later thawed, sonicated on ice for 30 seconds per tube using a cup-horn sonicator, and clarified by centrifugation at 1000×g for 10 minutes at 4° C. Aliquots of the supernatants were removed for plaque assay. The results of the plaque assay, conducted as described in EXAMPLE 1, are presented in FIG. 1.

The data presented in FIG. 1 confirms several conclusions:

1. Pre-infection incubation of cells with 50 mM sucrose is very beneficial for the final VZV yield. In each medium, EMEM or SRFE-2, VZV yields were higher when cells were treated with sucrose prior to infection. At 72 hours post-infection, the VZV yield in SRFE-2 grown cells exposed to sucrose yielded about sixteen times the VZV yield, measured as PFU, than did cells in minimal media without sucrose!

2. The provision of rich media (SRFE-2 plus soybean lipids during growth and SRFE-2 during vital growth) is beneficial to the VZV yield, but in conjunction with the sucrose effect, enables an order of magnitude more VZV to be produced. Thus, the rich medium appears to act synergistically with the sucrose effect.

3. The time of VZV harvest is very significant. Even under the optimized culture conditions, SRFE-2 and sucrose etc, the peak VZV yield is not achieved by 48 hours post-infection. At that point, only a four fold increase over minimal medium yield is achieved. However, at 72 hours post-infection, there is about a 16 fold increase in VZV yield.

In separate experiments, the VZV yield was not enhanced as much if 50 mM sucrose was added at the time of infection, rather than 72 hours prior to infection, thus indicating the importance of a long pre-infection phase for intracellular accumulation of sucrose. We also found that addition of 25 mM or 100 mM sucrose was less beneficial than 50 mM sucrose. The same approximate concentrations are applicable to lactose, cellobiose and maltose.

EXAMPLE 8

Effects of Multiple Enhanced Process Parameters on VZV Yield

A roller bottle experiment was done to determine the effects of various process changes (culture medium, sucrose supplementation, addition of $NH_4Cl$ to the stabilizer, Douncing or sonicating for virus release from cells) on cell-free VZV PFU yields. Cultures were planted at $80 \times 10^3$ cells/mL × 125 mL EBME, 10% FCS per roller bottle. These were adjusted to 425 mL with EBME or refed with SRFE+soy lipid medium, and infected with working seed VZV in 125 ("low volume") or 425 ("high volume") mL EMEM or SRFE medium (without soy lipid). The timing for these medium changes/infection was as described in Example 7. At various times before infection (96, or 24 h before infection, or at the time of infection), sucrose (suc) was added to 50 mM. Cultures receiving sucrose prior to infection also received sucrose in the virus infection medium. All cultures were infected at an approximate MOI=1:15 with VZV infected cells in EMEM cultures were harvested at 46 h in post-infection stabilizer containing 20 mM NH4Cl (N), or no supplement. All samples were frozen at −70° C., and virus was subsequently released from cells by either sonication or DOUNCE homogenization. All samples were clarified by centrifugation at 1000 g for 10 min.

The PFU results achieved for SONICATED samples permitted the following conclusions:

1. The use of the "high" medium volume of EMEM increased VZV PFU 2-fold. With SRFE, it appears here and in other experiments that optimal PFU yields are achieved near the "low" medium volume. In some cases, the yields at the "high" medium volume are suppressed., 2. NH4Cl is not critical for high PFU recoveries, 3. Sucrose increased PFU yields 2-fold for EBME/EMEM and 5-fold for SRFE cultures. There appears to be an effect of the time of sucrose addition on PFU. In another arm of this experiment, PFU yields were $94 \times 10^3$ for SRFE+soy/SRFE cultures not receiving sucrose and $296 \times 10^3$, $427 \times 10^3$, and $671 \times 10^3$, for cultures receiving sucrose at infection, 24 h before infection, and 96 h before infection respectively.

4. The sucrose treated cultures showed significantly less cytopathic effects than their sucrose-free counterparts. In another experiment, sucrose-treated cultures still didn't show degenerative cytopathic effects 1 week after infection, while their sucrose-free controls were completely lysed. It is possible therefore that the sucrose treated cells will accumulate more VZV (antigen and especially PFU) at extended incubation times (beyond the 46 h harvest from the roller bottle experiment).

5. The MOI was not adjusted in this experiment for higher cell concentrations at the time of infection due to cell growth in SRFE medium. Thus, even greater PFU yields could be obtained if this parameter were optimized.

EXAMPLE 9

Yield of Cell Free VZV Achieved by Mechanical Shear, Sonication and a Combination of These A large scale experiment was performed using multiple different conditions for VZV production, similar to the experiment described in EXAMPLE 8. A new parameter, the manner of cell disruption, was analyzed in this experiment. Results are reported below comparing cell-free VZV yield achieved by DOUNCE homogenization alone, sonication alone, and a combination of DOUNCE and sonication. The VZV culture conditions reported are for cells grown in minimal media (EBME/EMEM) or high nutrition (SRFE-2 plus soybean lipids/SRFE-2 plus 50 mM sucrose in the pre-infection phase). Cells were grown and harvested as described in EXAMPLE 8, and VZV pfu/mL was determined by the assay described in EXAMPLE 1:

From this data, it is clear that a substantial enhancement of VZV yield is achievable when mechanical shear is combined with sonic disruption of cells.

EXAMPLE 10

Figure 4:
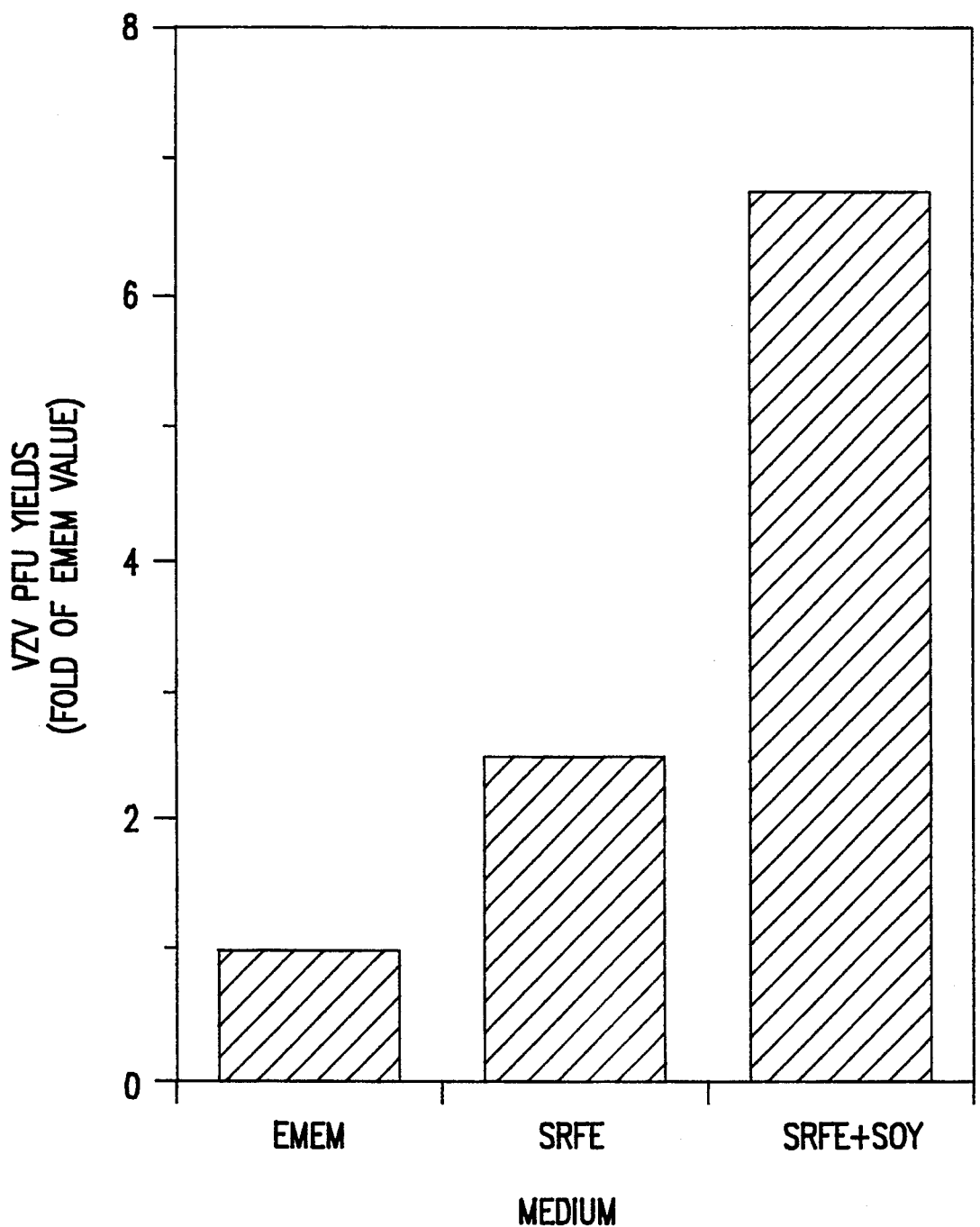
FIG. 4. VZV PFU Yields Achieved Using Different Culture Media.

Application of SRFE-2 Medium and Soybean Lipid Supplement to Achieve Increased Recovery of Live Varicella Vaccine from MRC-5 Cells MRC-5 cells were inoculated into 25 cm$^2$T-flasks in EBME and incubated for 3 days at 35° C. Medium was removed, and replaced with 12.5 mL of fresh EMEM medium, or SRFE-2 medium with 10% FCS, neomycin, glutamine, and either no soybean lipid or a 1:200 dilution of lipid. Cultures were incubated an additional 3 days at 35° C. Media were then removed, and cells received VZV infected MRC-5 cells and 12.5 mL volumes of 2% fetal calf serum, neomycin, glutamine in EMEM or SRFE-2. The culture condition indicated "SRFE-2" received SRFE-2 during cell culture and virus culture. The "SRFE+soy" condition indicates samples receiving SRFE-2 medium and a 1:200 dilution of soybean lipid during cell culture, but only SRFE-2 medium during virus culture. After culture for 48 hours, media were removed, cells were rinsed 4 times with 5 mL volumes of PBS and scraped into 1.2 mL volumes of stabilizer. Samples from duplicate flasks were pooled and frozen at −70° C. After subsequent thawing, cells were disrupted by sonication, clarified by centrifugation (1000 g for 10 min), and supernatants were frozen at −70° C. for subsequent assay of virus infectivity titers. Results are shown in FIG. 4. Conclusions: Use of SRFE-2 medium instead of EMEM resulted in a 2.5-fold increase in recovery of live varicella. Use of soybean-supplemented SRFE-2 during cell culture allowed an additional 2.7-fold increase in virus recovery, for a net 7-fold increase above that achieved using the EMEM virus growth process.

EXAMPLE 11

Competititve Elisa for Quantitation of VZV Antigen

Because the VZV plaque assay is time consuming, it is not particularly amenable to in-process control. A rapid VZV antigen ELISA permits measurement of VZV antigen amounts to permit monitoring of virus growth during manufacture of live varicella vaccine. Additionally, this test can be used to estimate VZV antigen amounts in clarified, sonicated vaccine bulks, and potentially to measure antigen in filled lyophilized vaccine vials. Briefly, this assay is conducted by incubation of VZV antigen from test samples with anti-VZV serum in solution. Remaining free antibody is allowed to bind to VZV antigen immobilized on ELISA microtiter plates. The amount of antibody capable of binding to the plates is inversely proportional to the amount of antigen in the test sample. Antibody binding to the plates is quantitated by reaction with an enzyme-linked anti-human antibody and appropriate substrate to pro-

TABLE 4

| | Cell-Free PFU/mL ($\times 10^{-3}$) | | | |
|---|---|---|---|---|
| Condition | DOUNCE | SONICATED DOUNCE PELLET | TOTAL | SONICATED ONLY |
| EBME/EMEM | 42 | 7 | 49 | 38 |
| EBME/EMEM | 64 | 4 | 66 | 46 |
| SRFE 2 + sucrose, | 154 | 47 | 201 | 42 | vide a colored product which is quantitated spectrophotometrically.

The VZV antigen ELISA and the VZV plaque assays should generally provide correlative data, but it should be borne in mind that the VZV antigen assay detects non-viable as well as viable VZV. Since the immune response generated by killed VZV has not been shown to be as effective as the response to live attenuated virus, the plaque assay is the critical assay for determination of viral inoculum dose for VZV vaccines. However, the antigen assay is also valuable in that it provides a measure of the total antigen load being administered to a VZV vaccine recipient.

Test Procedure

1. ELISA plates are coated with glycoproteins (gps) from VZV-infected or uninfected MRC-5 cells, and are overcoated with 1% bovine serum albumin [fraction V, #A-9647, Sigma], 0.1% $NaN_3$) to reduce non-specific adsorption of antibodies to the plates. Alternating rows are coated with VZV or control antigen (i.e. rows A, C, E, and G receive VZV gp and rows B, D, F, and H receive uninfected MRC-5 gp antigen).

2. Clarified (3250 g-min) test antigen is diluted in stabilizer in 12×75 mm tubes or microtubes. A standard virus antigen preparation (26 units/mL VZV antigen by dot blot assay) is diluted 1:10 and then serially 1:1.25-fold to provide antigen concentrations of 2.6, 2.1, 1.7, 1.3, 1.1, 0.9 units/mL. Additional dilutions may be included to provide 0.7 and 0.5 units/mL of antigen. This dilution series is used to generate a standard curve for the measurement of antigen amounts in test samples.

3. A human anti-VZV serum is diluted in stabilizer to 2 times the final desired dilution.

4. Three hundred μl volumes of diluted antigen are dispensed into microtubes, mixed with 300 μl diluted anti-VZV serum and incubated at 35° C. for 15-22 min. A control includes human anti-VZV and diluent (no antigen).

5. Aliquots of 100 μl from each serum-antigen mixture are added to 2 replicate VZV glycoprotein (VZV gp) coated wells and 2 MKC-5 gp coated wells (4 wells per sample) (e.g.: sample 1 in column 1, rows A, B, C, and D; sample 2 in column 2, rows A, B, C, and D; etc.).

6. Plates are incubated for 15±1 minute at 35° C. to allow free antibody (not complexed to antigen in solution) to bind town, virus antigen immobilized on the plates.

7. Unbound antibody is removed by washing and wells receive an alkaline phosphatase conjugated goat anti-human IgG to detect bound human antibody.

8. After incubation for 15±1 minute at 35° C., unbound conjugate is removed by washing. Bound conjugate is detected by incubation for 15 min at 35° C. with p-nitrophenyl phosphate substrate dissolved in diethanolamine buffer.

9. After termination of the substrate reaction by addition of 50 μl/well 3M NaOH, color development (OD at 405 nm) is quantitated using a microplate spectrophotometer.

Test Calculations and Interpretation

1. Respective replicate OD values for the replicate VZV and MRC-5 coated wells are averaged. Experience has shown the MRC-5 OD to be consistent between different samples and dilutions. Therefore, the MRC-5 values for the entire plate are averaged and used to correct for non-specific binding of the primary antibody or conjugate to uninfected cell extracts. The averaged MRC-5 OD is subtracted from the respective averaged VZV ODs to provide VZV-specific OD (ΔOD) values.

2. Generation of a standard curve for measurement of antigen amounts: The standard curve ΔOD values are plotted against the known antigen concentrations (units VZV/mL).

The data are entered into an appropriate graphics program (e.g.: Cricket Graph version 1.3, Cricket Software, Malvern, Pa.), the linear portion of the curve is identified (must include at least 4 points), and the "line fit formula" (y=a+bx) is obtained.

3. Calculation of antigen amounts of test samples: Values for a and b are given by the line-fit formula, and y (ΔOD) is known. The remaining unknown value, x, representing the units/mL antigen, can then be calculated, and corrected by the sample dilution to obtain the antigen concentration of the undiluted sample. A sample general calculation follows:

| Sample antigen | Dilution | ΔOD | units/mL antigen from line formula | units/mL corr for |
|---|---|---|---|---|
| dilution A | 1:2 | Y | X=(y−a)/b | |
| | | | | (x)*(dil factor) |

The reported antigen concentration is that obtained with the least diluted sample providing a ΔOD value within the linear portion of the standard curve.

EXAMPLE 12

VZV Antigen Elisa and Comparison with VZV PFU Yield

Figure 2:
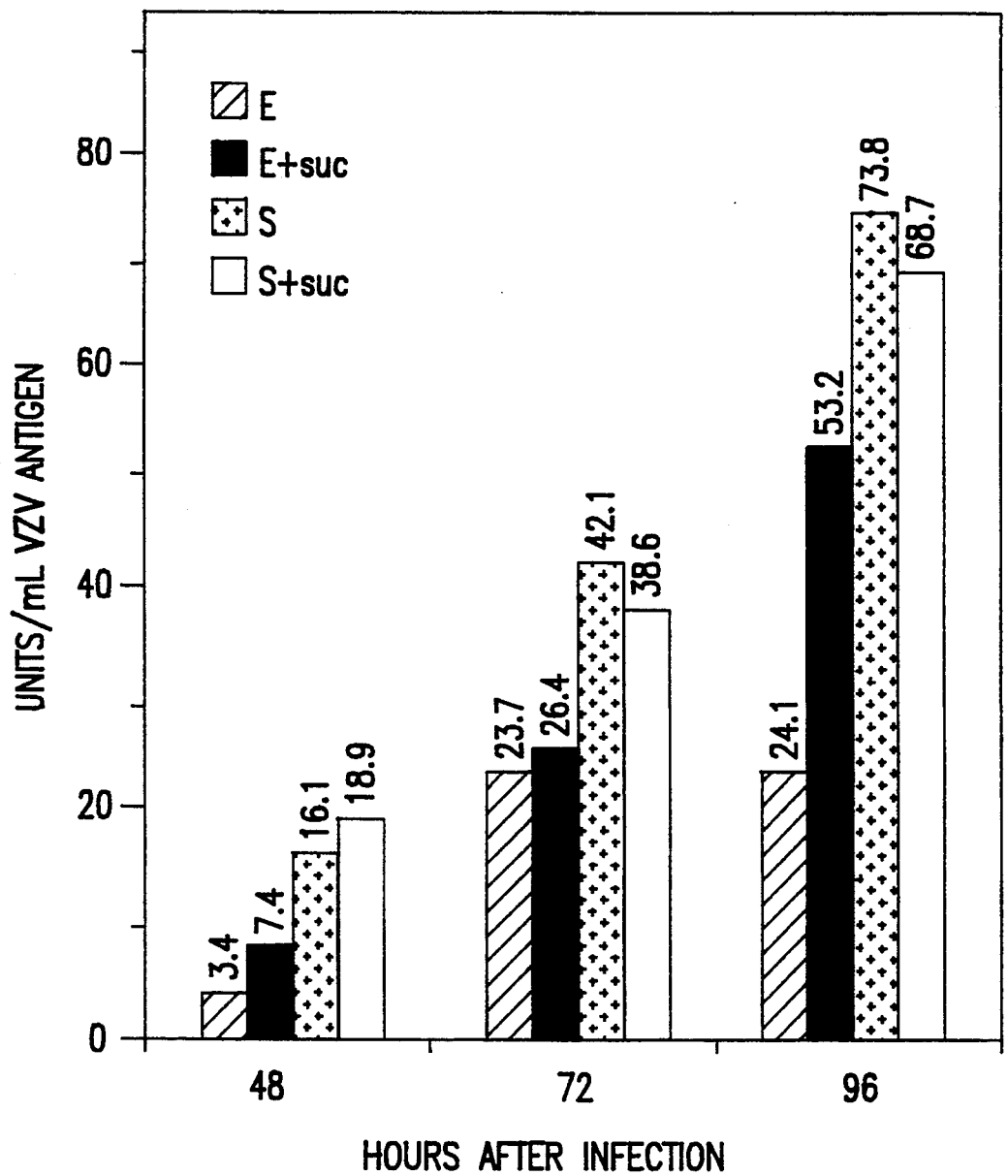
FIG. 2. Cell-Free VZV Antigen Yields

The samples of cell-free VZV generated EXAMPLE 7 for which PFU/mL yield is presented in FIG. 1 were assayed according to the VZV antigen ELISA presented in EXAMPLE 11. The results of this assay are presented in FIG. 2.

It is notable that the VZV antigen continues to climb at 96 hours even though, according to the FIG. 1 data, the PFU/mL is declining. It is also notable that the the VZV antigen level in SRFE-2 plus soy plus sucrose is nowhere near 16-fold the antigen level in EMEM (FIG. 2), yet the viable cell-free VZV pfu/ml is (FIG. 1). From this comparison, it appears that the sucrose effect is a major contributor to maintainance of viable VZV at 72 hours post infection.

EXAMPLE 13

Enhancement of MRC-5 cell growth using SRFE-2 medium and a soybean lipid supplement MRC-5 cells were inoculated in 25 $cm^2$T-flasks at 53,000 cells/mL in 12.5 mL volumes of EBME, 10% FCS, 50 μg/mL neomycin, and 2 mM L-glutamine, and incubated at 35° C. After 2-3 days, medium was removed and replaced (shift 2) with 12.5 mL of fresh medium or SRFE-2 medium containing 10% FCS, 50 μg/mL neomycin, 2 mM L-glutamine, and different amounts of soybean lipid. Undiluted soybean lipid contained 20 mg/mL lipid and 100 mg/mL bovine serum albumin.

Media were removed at 6 days after initial cell planting, and replaced with 12.5 mL volumes of 2% FCS, 50 μg/mL neomycin, 2 mM L-glutamine in EMEM, or SRFE-2 medium supplemented with different amounts of soybean lipid. Cells were dissociated from selected flasks by trypsin treatment and cells were counted in a hemacytometer. Cell counts were determined for remaining cultures after an additional 2 days of culture at 35° C., and a summary of the results is presented in Table 5.

TABLE 5

Use of SRFE Medium and Soybean Lipids to Enhance MRC 5 Cell Densities

| MEDIUM | Expt. 1 | Expt. 2 |
|---|---|---|
| EMEM (E) | 2.3 | 1.5 |
| SRFE (S) | 4.0 | 3.8 |
| S + 1:100 soy | D | 7.6 |
| S + 1:200 soy | 7.9 | 7.6 |
| S + 1:500 soy | 5.9 | 3.7 |
| S + 1:2000 soy | 5.0 | 3.8 |

Medium shift 1=medium replaced with indicated medium supplemented with 10% FCS 2–3 days after cell planting.

Medium shift 2=medium replaced with indicated medium supplemented with 2% FCS 6 days after cell planting.

ND=not determined.

Conclusions: Use of SRFE-2 medium without a lipid supplement resulted in an approximate 2-fold increase in cell numbers over that achieved in EMEM alone. Cell yields were further increased, in a dose dependent fashion, by supplementation of medium with soybean lipid. Maximal cell yields were achieved using the combination of SRFE-2 medium and about 200–400 µg/mL of lipid.

EXAMPLE 14

Growth of WI-38 Cells According to the Process of This Invention

WI-38 cells were inoculated into 25 cm$^2$T-flasks at 53,000 cells/mL in 12.5 mL volumes of EBME, 10% FCS, 50 mg/mL neomycin, and 2 mM L-glutamine, and incubated at 35° C. After 2 days, medium was removed, and replaced with 12.5 mL of SRFE-2 medium supplemented with 50 mg/mL neomycin, 2 mM L-glutamine, and a 1:200 dilution of soybean lipid. Controls received medium without a lipid supplement. After 5 days of culture at 35° C., medium was removed, cells were dissociated from flasks by trypsin treatment, and counted in a hemacytometer. Remaining flasks were held for an additional 3 days prior to counting cells. A summary of the results follows:

TABLE 6

| Cell line | Lipid Supplement | cells/flask × 10$^{-6}$ after 5 days | cells/flask × 10$^{-6}$ after 8 days |
|---|---|---|---|
| 1 | − | 4.2 | 4.8 |
|   | + | 9.5 | 10.2 |
| 3 | − | 4.1 | 4.9 |
|   | + | 9.3 | 12.5 |

Conclusion: Supplementation of rich culture media with soybean lipid increased WI-38 cell yields by approximately 2-fold. Use of this cell line for VZV production is thus expected to proceed similarly to use of MRC-5 cells.

EXAMPLE 15

Procedure for Evaluation of MRC-5 Cell Growth Enhancement

MRC-5 cells are planted in 25-cm$^2$ T-flasks at about 53,000 cells/mL in 12.5 mL volumes of Basal Medium Eagle with Earle's Salts (EBME), 10% FCS, 50 µg/mL neomycin sulfate (neo) and 2 mM glutamine (Gln). Cultures are incubated at 35° C. for 3 days, by which time cell monolayers are typically about 50–75% confluent. Medium is removed and replaced with 10 to 12.5 mL volumes of 10% FCS, 50 μg/mL neo and 2 mM Gln±soybean or other lipid, in SRFE-2 medium, and cultures are returned to incubation at 35° C. Cell counts are determined at various times by trypsinizing cells (2.5 mL volumes of 0.25% citrate trypsin solution) and counting in a hemacytometer.

Cell viability is monitored by cell exclusion of 0.2% trypan blue. Cell counts are used to derive a cell concentration which in turn is corrected for the total vlume of cell suspension to obtain the cell yield per flask. In some experiments, cultures are shifted into medium with 2% FCS 3–4 days after replacement of medium, and cell counts are determined after incubation for an additional 2 days.

EXAMPLE 16

Effect of Prolonged Exposure of Cultured Cells to Lipid Supplements

MRC-5 cells were planted in T25 flasks, fed after 3 days (first refeed), and cell counts were determined after an additional 3 days of growth. Additional T25 flasks were allowed to continue growth by refeeding ±lipid (second refeed), and allowed to grow an additional 2 days. Cells were recovered with trypsin. Yields were 2.6×$10^6$ for cells planted in EBME and grown in EMEM, while cells grown in SRFE-2 plus 1:100 dilution of soybean lipids reached 6.6×$10^6$ and 7.7×$10^6$. Cells grown the additional 2 days yielded 2.76×$10^6$ for EBME/EMEM grown cells while EBME/SRFE-2, no soybean lipid supplementation, yielded 9.2×$10^6$ and 7.88×$10^6$ cells per T25 flask. EBME/SRFE-2+1.100 soybean lipid grown cells yielded only 2.48 and 2.28×$10^6$ cells. This data indicates that prolonged exposure (about 5 days after the second refeed) to high lipid concentrations may eventually lead to reduced cell yields, presumably due to cell death. Thus, in general, cells are refed with rich medium absent lipid supplementation. This switch to a lipid-free, rich medium is particularly important when a viral growth phase is initiated as the lipid may be toxic to viral growth or continued cell viability in the presence of viral onslaught.

EXAMPLE 17

Effects of Different Lipid Concentrations on Cell Growth in Rich and Minimal Media Following essentially the same procedure and refeed/cell quantitation schedule described in Example 16 for MRC-5 culture, the following cell yields, were achieved (note: the + and – symbols after the medium description indicates presence or absence of the indicated amount, in mg/mL of soybean lipid (sl.) supplementation in the second refeed medium):

| Medium | Total T25 Flask MRC-5 cell yield × $10^{-6}$ Days after 2nd refeed | |
| --- | --- | --- |
| | 3 | 5 |
| EBME/EMEM (3 expts.) | 4.3; 2.46; 1.52 | 2.94; 3.50 |
| EBME/SRFE 2 | 3.80 | |
| EBME/SRFE 2 − 0.4 sl. | | 13.69; 11.09 |
| EBME/SRFE-2 + 0.4 sl. | 11.7 | 11.65 |
| EBME/SRFE 2 − 0.2 sl. | 5.10 | 8.51; 6.27 |
| EBME/SRFE 2 + 0.2 sl | 7.62; 9.7 | 9 66 |
| EBME/SRFE-2 − 0.1 sl. | 3.52 | |
| EBME/SRFE 2 + 0.1 sl. | 4.94 | |
| EBME/SRFE-2 − 0.04 sl. | 3.10 | |
| EBME/SRFE-2 + 0.04 sl. | 3.16 | |
| EBME/SRFE-2 − 0.01 sl. | 2.90 | |
| EBME/SRFE 2 + 1:01 sl. | 3.82 | |

The data summarized above are generally consistent with the observation noted in EXAMPLE 16 that prolonged exposure of cells to high lipid concentrations is not very beneficial, although the toxic effect noted in EXAMPLE 16 is less pronounced in this data. At lower lipid concentrations, longer cell exposure to lipid is less harmful and may be beneficial to increased yield of cells/$cm^2$ of growth surface.

EXAMPLE 18

Effect of Fetal Calf Serum Concentration on Cell Yields

The addition of 2% or 10% fetal calf serum in the presence of lipid supplements was tested in this experiment. MRC-5 cells were planted in EBME, refed 3 days later with SRFE-2 supplemented with different amounts of soybean lipid, refed 2 days later with the same concentration of lipid in SRFE-2 as provided in the first refeed. Cell yields in 10% FCS were 9.5, 11.3, and 12.2×$10^6$ for cultures supplemented with 0.1, 0.2, and 0.4 mg/mL lipid respectively. Where 2% FCS was provided, the cell yields were 6.5, 8.8, and 3.2×$10^6$ respectively. This experiment points out the beneficial effect on cell growth of provision of FCS supplementation as well as lipid supplementation. Whatever toxic effects the cells experience at elevated lipid concentrations is attenuated by provision of sufficient FCS supplementation.

EXAMPLE 19

Effects of Different Lipid Supplements on MRC-5 Cell Growth

MRC-5 cells were planted in T25 flasks in EBME. On day 3, cells were refed with SRFE-2 medium containing 10% FCS, supplemented with different lipid supplements. Boehringer Mannheim soybean lipid, Sigma cholesterol-rich lipids from adult bovine serum, or Miles/Pentex EX-CYTE I or Very Low Endotoxin bovine lipoprotein were provided at the indicated concentrations. Cell counts at refeed were, in millions: 1.19. Five days later, cells were counted. Cells in EMEM were 2.97; in SRFE-2, or SRFE-2 plus 0.4 mg/mL, 0.2 mg/mL, and 0.1 mg/mL with soybean lipids generated 4.83, 10.44, 8.67, and 8.04 million cells respectively. EX-CYTE I at 1:50, 1:100, 1:200 generated 5.37, 4.80, and 4.74 million cells respectively. EX-CYTE VLE at 1:25, 1:50, 1:100 gave rise to 5.49, 7.23, and 7.92 million cells respectively. Sigma high cholesterol lipids at 1:25, 1:50, 1:100 gave rise to 6.87, 7.56, and 7.65 million cells respectively. The Boehringer Manneheim soybean lipids offered the greatest cell yield enhancement, although EX-CYTE VLE and Sigma lipids were almost as effective. The enhancement effect is therefore not unique to soybean lipids.

What is claimed is:

1. A process for preparing a live varicella zoster virus (VZV) vaccine which comprises the steps in the following order:
    a. Culturing VZV infection-susceptible cells, selected from human diploid cells, to confluency in monolayer culture, under conditions of sufficiently high nutrition to achieve a high degree of cell replication, and supplying a non-metabolizable disaccharide;
    b. Infecting the cells cultured according to step (a) at as close to the point of confluency as possible with as high a multiplicity of infection of VZV-infected cells as practical;
    c. Maintaining the VZV-infected culture in a state of high nutrition for about 22–96 hours and harvesting at the point of peak infectious VZV production;
    d. Washing the VZV-infected culture with a physiologic solution, optionally containing a lysosomotropic agent, such as ammonium chloride or chloroquine, prior to harvesting the VZV infected cells;
    e. Harvesting the VZV infected cells into a minimal volume of a stabilizing solution and either disrupting the cells immediately or freezing the cells for later disruption;
    f. Disrupting the VZV-infected cells to optimally release cell-associated VZV, and removing cellular debris, to provide a cell-free VZV preparation.

2. A process for preparing a live, attenuated, cell-free varicella-zoster virus (VZV) vaccine which comprises the steps in the following order:
    a. Culturing VZV infection-susceptible cells to confluency, wherein said culturing comprises:
        1. a cell planting phase,
        2. a cell growth phase either in as large a volume of minimal medium as practical or a lesser volume of high nutrition medium, and
        3. a pre-infection phase comprising exposure of the cells to a non-toxic, non-metabolizable disaccharide;
    b. Infecting the cells cultured according to step a at as close to the point of confluency as possible with as high a multiplicity of infection of attenuated VZV-infected cells as practical;
    c. Maintaining the VZV-infected culture in a large volume of minimal medium or a smaller volume of rich medium for 22–96 hours to the point of peak VZV production by rapid VZV antigen Eliza;
    d. Washing the VZV-infected culture with a physiologic solution optionally containing a lysosomotropic agent prior to harvesting;
    e. Harvesting the VZV-infected culture by
        1. removing liquid,
        2. adding a minimal volume of stabilizer solution,
        3. scraping or chemically liberating the VZV-infected cells,
        4. optionally freezing the liberated VZV-infected cells at about −70° C.;
    f. Disrupting the liberated VZV-infected cells to optimally release cell-bound VZV, and removing cellular debris, and optionally lyophilizing the cell-free VZV or storing in liquid frozen form.

3. The process of claim 1 wherein the VZV-infection susceptible cells are MRC-5 cells, the attenuated VZV is the Oka strain of varicella zoster virus, and the culture temperature is between about 30°–37° C.

4. The process of claim 3, wherein the disaccharide is sucrose provided at about 20–60 mM, and the culture temperature is about 35° C.

5. The process of claim 4 wherein the MOI is between about 1:25 and 1.625.

6. The process of claim 5 wherein the lysosomotropic agent is ammonium chloride provided at between about 20–50 mM or chloroquine, provided at about 230 µM.

7. The process of claim 6 wherein the high nutrition medium is the medium SRFE-2 optionally supplemented with about 0.02–0.4 mg/ml soy-lipids.

8. The process of claim 7 wherein the virus is released from cells by sonication or DOUNCE homogenization, or both.

9. A process for preparing a live, attenuated, cell-free varicella-zoster virus (VZV) vaccine which comprises the steps in the following order:
   a. Culturing MRC-5 cells to confluency, wherein said culturing comprises:
      1. a cell planting phase in EBME,
      2. a cell growth phase in the medium SRFE-2 supplemented with about 0.2 mg/ml soy-lipids, starting about 3 days after cell planting,
      3. a pre-infection phase, comprising exposure of the MRC-5 cells to 20–50 mM sucrose for about 24–96 hours pre-infection;
   b. Infecting the cells cultured according to step a at as close to the point of confluency as possible with as high a multiplicity of infection of attenuated VZV-infected MRC-5 cells as practical;
   c. maintaining the VZV-infected culture for about 37–96 hours and harvesting at the point of peak VZV production by rapid VZV antigen Eliza;
   d. washing the culture with phosphate buffered saline optionally supplemented with 1–100 mM NH$_4$Cl or chloroquire;
   e. harvesting the VZV-infected MRC-5 cells by:
      1. removing liquid,
      2. adding a minimal volume of stabilizer optionally containing about 1–100 mM NH$_4$Cl, or chloroquine at about 230 µM;
      3. scraping the cells or liberating the cells chemically,
      4. optionally freezing the liberated VZV-infected cells at −70° C.;
   f. Disrupting the liberated VZV-infected cells by 1. DOUNCE homogenization, 2. pelleting debris and retention of the supernatant, 3. sonicating the pellet and repelleting, and 4. combining and retaining the supernatants from steps f-2, and f-3;
   g. Diluting the product of step (f) in stabilizer and filling the product into unit doses for lyophilization and storage at 4° C. or lower such that no lower than about 1000 PFU is available per dose at the time of later use.

* * * * *